United States Patent [19]

Danho et al.

[11] Patent Number: 5,013,722

[45] Date of Patent: May 7, 1991

[54] CHOLECYSTOKININ ANALOGS FOR CONTROLLING APPETITE

[75] Inventors: Waleed Danho, Wayne; Vincent S. Madison, Mountain Lakes; Joseph Triscari, Bloomfield, all of N.J.

[73] Assignee: Hoffmann-LaRoche Inc., Nutley, N.J.

[21] Appl. No.: 400,177

[22] Filed: Aug. 25, 1989

Related U.S. Application Data

[63] Continuation of Ser. No. 65,241, Jun. 22, 1987, abandoned, which is a continuation-in-part of Ser. No. 871,721, Jun. 6, 1986, abandoned.

[51] Int. Cl.[5] .................. A61K 37/24; C07K 7/06
[52] U.S. Cl. ........................ 514/16; 514/17; 530/328; 530/329
[58] Field of Search ............. 530/328, 329; 514/16, 514/17

[56] References Cited

U.S. PATENT DOCUMENTS 4,400,377  8/1983  Zetler et al. ................. 514/66
4,490,364 12/1984  Rivier et al. ................. 514/16
4,517,180  5/1985  Yanaihara et al. ............. 514/16

OTHER PUBLICATIONS

Durieux et al., Peptides Structure and Function, Deber et al., (ed.), Pierce Chemical Co., Rockford, Ill., pp. 575–578 (1985).
Durieux et al., Peptides, vol. 6, pp. 495–501 (1985).
Najdovski et al., Neurochem. Int., pp. 459–465 (1987).
Mutt et al., Biochem. J., vol. 125, pp. 57–58 (1971).
Jorpes et al., Acta. Chem. Scand., vol. 18, pp. 2408–2410 (1984).
Della-Fera et al., Science, vol. 206, pp. 471–473 (1979).
Morley, Life Sciences, vol. 30, pp. 485–488 (1982).
Pluscec et al., J. Medicinal Chem., vol. 13, pp. 349–352 (1970).
Penke et al., J. Med. Chem., vol. 27, pp. 845–849 (1984).

*Primary Examiner*—John Doll
*Assistant Examiner*—Christina Chan
*Attorney, Agent, or Firm*—George M. Gould; William H. Epstein; Bruce A. Pokras

[57] ABSTRACT

Cholecystokinin analogs useful for suppressing food intake in mammals and humans.

22 Claims, 1 Drawing Sheet

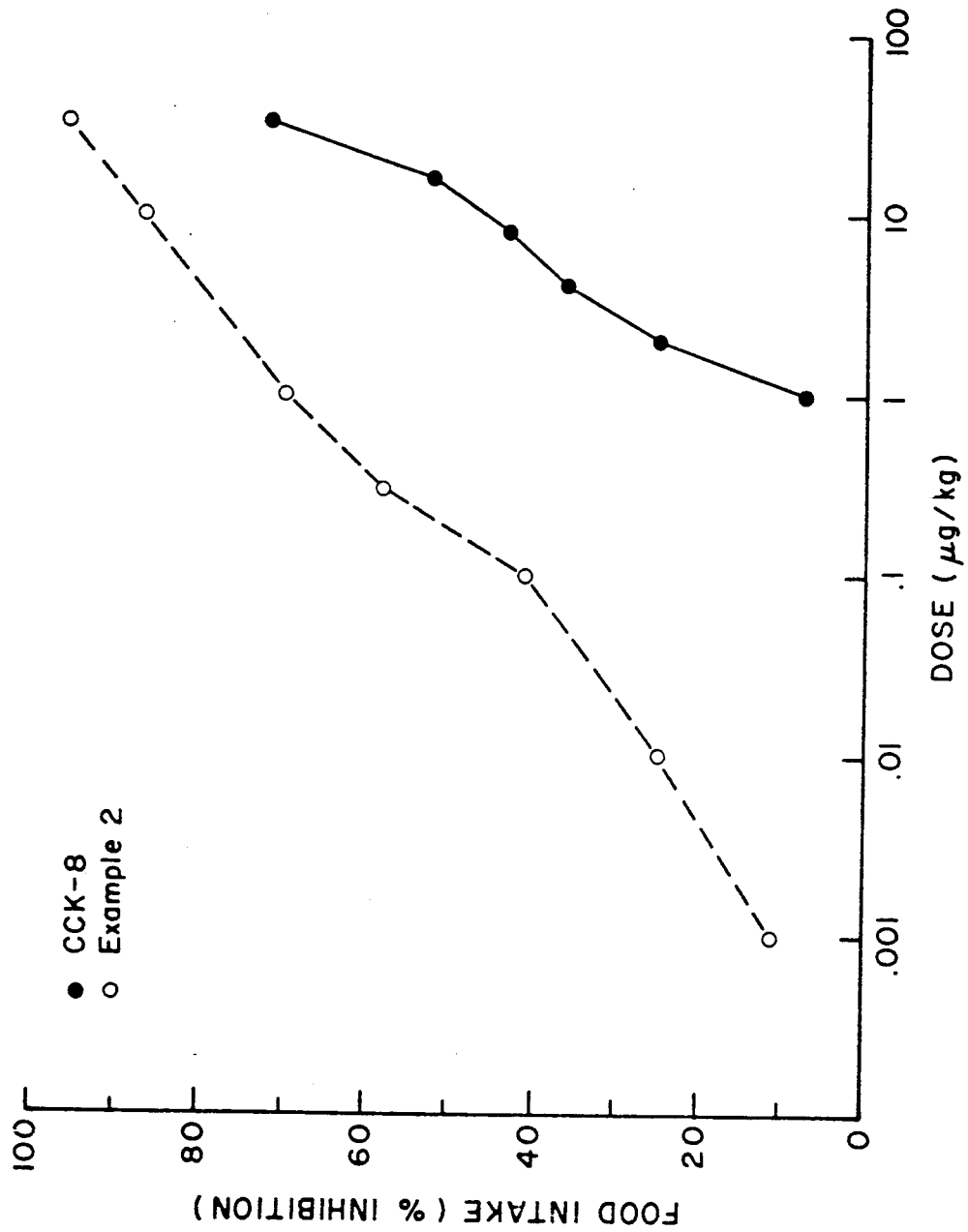

CHOLECYSTOKININ ANALOGS FOR CONTROLLING APPETITE

CROSS-REFERENCE TO RELATED APPLICATIONS

This application is a continuation of U.S. Ser. No. 065,241 filed June 22, 1987, now abandoned, which in turn is a continuation-in-part of U.S. Ser. No. 871,721 filed June 6, 1986, now abandoned.

BACKGROUND OF THE INVENTION

There are approximately 34 million Americans at least 20 percent above their desirable weights for whom treatment is advisable, according to the conclusions reached by a recent NIH concensus conference. (National Institutes of Health consensus Panel Report, Feb. 13, 1985; See also *Science,* 1985, 207: 1019–1020.)

In these individuals obesity is a contributory factor to the increased incidence of cardiovascular disease, hypertension, hypercholesterolemia, non-insulin dependent diabetes (NIDD) and cancers of the uterus, breast, gallbladder, colon, rectum and prostate. In addition obesity has a negative weight related impact on mortality; such that in extreme or morbid obesity the mortality ratio may be 1200 percent above normal.

Weight reduction is often recommended as the first course of action for patients suffering from NIDD, hypertension, hypercholesterolemia, coronary artery heart disease, gout and osteoarthritis. However, there are relatively few therapeutic tools which the physician can use to accomplish weight loss. Pharmaceutical agents which are currently used as adjuncts to dietary counseling are effective for short term therapy, but are unacceptable for long term use because of the development of tolerance, their CNS activity and undesirable side effects. Thus, approximately 95% of those patients who successfully lose weight regain to their initial body weights within 12 to 84 months. An agent which reduces food intake by mimicking the body's own peripheral satiety signals would be expected to be more successful for use in chronic therapy, have a more desirable side effect profile and have less CNS activity.

Cholecystokinin (CCK) is a polypeptide hormone which was first isolated as a 33-amino acid peptide from the porcine gastrointestinal tract. (Mutt et al, *Biochem J.,* 1971, 125: 57–58. Mutt et al., *Clin Endocrinol,* supplement, 1976, 5: 175–183.) Peripherally administered CCK has been shown to produce satiety in the rat and the monkey and infusions of CCK-8, the octapeptide analog of CCK, has been shown to decrease food intake in lean and obese men. G. P. Smith, *Int J Obesity* 1984, 8 Suppl 1:35–38: Jorpes et al, *Acta. Chem. Scand.* 1964, 18:2408; Della-Fera et al., *Science,* 1979, 206:471–73; Gibbs. et al., 1973, *J. Comp. Physiology and Psychology,* 84, 488–495. It is now accepted that CCK has satiety-inducing effects and thus., may be useful to reduce or suppress food intake in man.

The polypeptide hormone, CCK-33, has the amino acid sequence:

$$\underset{1}{Lys}-Ala-Pro-\underset{5}{Ser}-Gly-Arg-Val-Ser-\underset{10}{Met}-Ile-$$
$$\underset{15}{Lys}-Asn-Leu-Gln-Ser-Leu-Asp-Pro-Ser-\underset{20}{His}-$$
$$\underset{}{Arg}-Ile-Ser-Asp-\underset{25}{Arg}-Asp-Tyr(SO_3H)-Met-Gly-\underset{30}{Trp}-$$
$$Met-Asp-\underset{33}{Phe}-NH_2.$$

Fragments of CCK, e.g. CCK-8 and CCK-7 also have been shown to have satiety-inducing effects. CCK-8 has the amino acid sequence:

$$\underset{26}{Asp}-\underset{27}{Tyr(SO_3H)}-\underset{28}{Met}-\underset{29}{Gly}-\underset{30}{Trp}-\underset{31}{Met}-\underset{32}{Asp}-\underset{33}{Phe}-NH_2.$$

CCK-7 is one amino acid less than CCK-8, i.e., it is CCK-8 minus the 26-position Asp.

Various CCK-8 analogs are known. For example, U.S. Pat. No. 4,400,377 teaches the use of analogs of CCK-8 to treat pain. U.S. Pat. No. 4,490,364 discloses that analogs of CCK-8 stimulate the contraction of the gall bladder and assist the secretion of gastric acid. The psychodepressant use of CCK-8 analogs is disclosed by U.S. Pat. No. 4,517,180.

Although various analogs of CCK-8 are known, neither the CCK derivatives of the invention, nor their use to suppress food intake in animals is known. Further, although the naturally occurring peptides, CCK-33, CCK-8 and CCK-7 have satiety inducing effects, these peptides are short acting. Accordingly, it is an object of the invention to prepare CCK-analogs which exhibit satiety-inducing effects which are equal to or greater than the naturally occurring CCK-8 but which also have longer lasting effects.

SUMMARY OF THE INVENTION

The invention is directed to peptides of the formula I.
$X-(R)_n-Tyr(SO_3H)-R_1-R_2-R_3-R_4-R_5-N-methyl-Phe-Y$ wherein $$X = -\overset{O}{\underset{\|}{C}}-R_6, \ -\overset{O}{\underset{\|}{C}}-OR_6, \ -\overset{O}{\underset{\|}{C}}-(CH_2)_m-CH_3,$$
$$-\overset{O}{\underset{\|}{C}}-\overset{O}{\underset{\|}{C}}-OR_7, \ or \ -\overset{O}{\underset{\|}{C}}-(CH_2)_m-\overset{O}{\underset{\|}{C}}-OR_7$$

R = Asp or Aeg
$R_1$ = Met, Nle, Leu, Ile, or a bond
$R_2$ = Gly, Ala, D-Ala, or β-Ala
$R_3$ = Trp or Trp (For)
$R_4$ = Met, Nle or Nva
$R_5$ = Thr(SO$_3$H) or Ser(SO$_3$H), or Hyp(SO$_3$H)
$R_6$ = H or C$_{1-3}$ alkyl
$R_7$ = H or C$_{1-3}$ alkyl, or C$_{1-3}$ haloalkyl
$R_8$ = H or C$_{1-3}$ alkyl
Y = OR$_8$ or NR$_9$R$_{10}$
$R_9$ = H or C$_{1-3}$ alkyl
$R_{10}$ = H or C$_{1-3}$ alkyl
n = 0 or 1
m = 1–14

The invention is further directed to a method of suppressing food intake in mammals by administering to said mammal an effective food intake suppressing amount of the compounds of Formula I.

By mammal is meant any warm-blooded mammal including human beings.

ABBREVIATIONS USED

The following abbreviations or symbols are used to represent amino acids, active groups, protecting group and the like.

| Symbol | Meaning |
| --- | --- |
| Ac | Acetyl |
| Suc | Succinyl |
| Mal | Malonyl |
| For | Formyl |
| Aeg | Amino ethyl glycine |
| Boc | tert.-Butyloxycarbonyl |
| Boc-Aeg(Z)-OH | N-Benzyloxycarbonyl-N-(2-t-butyl-oxy carbonyl)amino ethyl glycine. |

Amino acids are given their commonly understood three-letter designation herein, and unless otherwise specified, the L-isomer is meant.

SUMMARY OF THE DRAWING

FIG. 1 illustrates that the peptide of Example 2 effectively suppresses food intake in rats at a lower dosage than does CCK-8.

DETAILED DESCRIPTION OF THE INVENTION

The invention is desired to peptides of the formula: I.
$X-(R)_n-Tyr(SO_3H)-R_1-R_2-R_3-R_4-R_5-N-methyl-Phe-Y$ wherein $$X = -\overset{O}{\underset{\|}{C}}-R_6, \quad -\overset{O}{\underset{\|}{C}}-OR_6, \quad \overset{O}{\underset{\|}{C}}-(CH_2)_m-CH_3,$$

$$-\overset{O}{\underset{\|}{C}}-\overset{O}{\underset{\|}{C}}-OR_7, \text{ or } \overset{O}{\underset{\|}{C}}-(CH_2)_m-\overset{O}{\underset{\|}{C}}-OR_7$$

R = Asp or Aeg,
$R_1$ = Met, Nle, Leu, Ile, or a bond
$R_2$ = Gly, Ala, D-Ala, or β-Ala
$R_3$ = Trp or Trp (For)
$R_4$ = Met, Nle or Nva
$R_5$ = Thr(SO$_3$H), Ser(SO$_3$H), or Hyp(SO$_3$H)
$R_6$ = H or $C_{1-3}$ alkyl
$R_7$ = $R_8$ = H, $C_{1-3}$ alkyl, or $C_{1-3}$ haloalkyl
$R_8$ = H or $C_{1-3}$ alkyl
Y = $OR_8$ or $NR_9R_{10}$
$R_9$ = H or $C_{1-3}$ alkyl
$R_{10}$ = H or $C_{1-3}$ alkyl
n = 0 or 1
m = 1–14

As used herein, the term "$C_{1-3}$alkyl" refers to methyl, ethyl, n-propyl and isopropyl. The term "halo" refers to chloro, bromo, fluoro or iodo. The term "halo($C_{1-3}$)alkyl" refers to such groups as chloromethyl, bromomethyl, trifluoromethyl, chloroethyl, dichloroethyl, chloropropyl, bromoethyl, iodomethyl and the like.

Preferred is a peptide of Formula I wherein X=Ac,$(R_n)$ where R=Aeg and n=1, $R_1$=Met, Nle, or a bond, $R_2$=Gly, D-Ala, or Ala; $R_3$=Trp(For); $R_4$=Met or Nle; $R_5$=Thr(SO$_3$H) and Y=NH$_2$ said peptide having the formula:

Ac—Aeg—Tyr(SO$_3$H)—R$_1$—R$_2$—Trp—(For)—R$_4$—Thr(SO$_3$H)—N—methyl—Phe—NH$_2$ Particularly preferred is a peptide of Formula I wherein X=Ac; $(R)_n$ where R=Aeg and n=1; $R_1$=Met; $R_2$=Gly; $R_3$=Trp (For); $R_4$=Met; $R_5$=Thr(SO$_3$H); and Y=NH$_2$ said peptide having the formula:

Ac—Aeg—Tyr(SO$_3$H)—Met—Gly—Trp For—Met—Thr(SO$_3$H)—N—methyl—Phe—NH$_2$  I(a)

Also preferred is a peptide of Formula I wherein X=Ac; $(R)_n$ where n=0; $R_1$=Met a bond or Nle; $R_2$=Gly; D-Ala or Ala; $R_3$=Trp or Trp(For); $R_4$=Met or Nle; $R_5$=Thr(SO$_3$H) and Y=NH$_2$.

Particularly preferred is a peptide of Formula I wherein X=Ac; $(R_n)$ where n=0: $R_1$=Met; $R_2$=Gly; $R_3$=Trp(For); $R_4$=Met; $R_5$=Thr(SO$_3$H); and $Y_2$=NH said peptide having the formula:

Ac—Tyr(SO$_3$H)—Met—Gly—Trp(For)—Met—Thr(SO$_3$H)—N—methyl—Phe—NH$_2$  I(b)

Particularly Preferred is a peptide of formula I wherein X=Ac $(R)_n$ where n=0, $R_1$=Met; $R_2$=Gly; $R_3$=Trp; $R_4$=Met; $R_5$=Thr(SO$_3$H); and Y=NH$_2$ having the formula Ac—Tyr(SO$_3$H)—Met—Gly—Trp—Met—Thr(SO$_3$H)—N—methyl—Phe—NH$_2$  I(c)

Particularly preferred is a peptide of Formula I wherein X=Ac; $(R_n)$ where n=0, $R_1$=Nle; $R_2$=D-Ala; $R_3$=Trp(For); $R_4$=Met; $R_5$=Thr(SO$_3$H); and Y=NH$_2$ said peptide having the formula:

Ac—Tyr(SO$_3$H)—Nle—(D)Ala—Trp(For)—Met—Thr(SO$_3$H)—N—methyl—Phe—NH$_2$  I(d)

Particularly preferred is a peptide of Formula I wherein X=Ac; $(R_n)$ where n=0; $B_1$=Nle; $R_2$=(D)Ala; $R_3$=Trp; $R_4$=Met; $R_5$=Thr(SO$_3$H) and Y=NH$_2$ and of the formula:

Ac—Tyr(SO$_3$H)—Nle—(D)Ala—Trp—Met—Thr(SO$_3$H)—N—methyl—Phe—NH$_2$  I(e)

Particularly preferred is a peptide of Formula I wherein X=Ac; $(R_n)$ where n=0; $R_1$=Met; $R_2$=Ala; $R_3$=Trp(For); $R_4$=Met; $R_5$=Thr(SO$_3$H) and Y=NH$_2$ said peptide having the formula:

Ac—Tyr(SO$_3$H)—Met—Ala—Trp(For)—Met—Thr(SO$_3$H)—N—methyl—Phe—NH$_2$  I(f)

Particularly preferred is a peptide of Formula I wherein X=Ac; $(R_n)$ where n=0; $R_1$=Met; $R_2$=Ala; $R_3$=Trp; $R_4$=Met; $R_5$=Thr(SO$_3$H); Y=NH$_2$ said peptide having the formula:

Ac—Tyr(SO$_3$H)—Met—Ala—Trp—Met—Thr(SO$_3$H)—N—methyl—Phe—NH$_2$  I(g)

Particularly preferred is a peptide of Formula I wherein X=Ac; $(R_n)$ where n=0; $R_1$=Nle; $R_2$=Gly; $R_3$=Trp; $R_4$=Nle; $R_5$=Thr(SO$_3$H); and Y=NH$_2$ said peptide having the formula Ac—Tyr(SO$_3$H)—Nle—Gly—Trp—Nle—Thr(SO$_3$H)—N—methyl—Phe—NH$_2$  I(h)

Particularly preferred is a peptide of Formula I wherein X=Ac; $(R_n)$ where n=0; $R_1$=a bond;

$R_2$=Gly; $R_3$=Trp; $R_4$=Met; $R_5$=Thr($SO_3H$) and Y=$NH_2$ said peptide having the formula Ac—Tyr($SO_3H$)—Gly—Trp—Met—Thr($SO_3H$)—N—methyl—Phe—$NH_2$     I(i)

The invention is further directed to a composition for suppressing food intake in animals comprising a food intake suppressing amount of the peptides of Formula I, or the pharmaceutically acceptable salts thereof. Still another aspect of the invention is directed to a method of suppressing food intake in mammals which comprises administering to said mammal a food intake suppressing effective amount of the peptides of Formula I or the pharmaceutically acceptable salts thereof.

As used herein the term "food intake suppressing amount" refers to the amount of peptide (on a weight basis) per Kg of body weight of the animal which must be administered to suppress food intake. It is within the skill of the art to calculate such amounts considering the method of administration, the particular animal and the weight of the animal. The level of skill in the art relating to the use of CCK-8 as a satiety agent is illustrated by the references summerized in the Morley, J. E., Minireview "The Ascent of Cholecystokinin (CCK) From Gut to Brain" Life Sciences, 1982, 479–493, 30.

The polypeptides of Formula I may be administered as water soluble salts, generally as salts of alkaline metals such as sodium or potassium salts, as alkylamine salts, preferably diethyl-amine salts or as acid addition salts, preferably the hydrochloride salt. The peptides of the formula I can be converted to pharmaceutically acceptable salts, such as salts of sodium, potassium and like alkali metals, salts of calcium and like alkaline earth metals, salts of triethylamine, ammonium and like amines, etc. by known methods.

Preparation of Peptides of Invention

The peptides of the invention may be prepared using solid phase synthesis by the method generally described by Merrifield, J. Am. Chem. Soc., 85:2149 (1963) although other eguivalent chemical synthesis known in the art may also be used. Solid-phase synthesis is commenced from the C-terminal end of the peptide by coupling a protected α-amino acid by an amide bond to a suitable resin, e.g., benzylhydrylamine (BHA) or (MBHA). BHA and MBHA resin supports are commercially available and generally used when the desired Peptide being synthesized has an unsubstituted amide at the C-terminal.

All solvents used in the preparations described herein, e.g. methylene chloride ($CH_2Cl_2$), 2-propanol, and dimethylformamide (DMF) were Burdick & Jackson "Distilled in Glass" grade and used without additional distillation. Trifluoroacetic acid (TFA), diisopropylethylamine (DIPEA), and dicyclohexylcarbodiimide (DCC) were Purchased from Chemical Dynamics Corp. and were "sequential" grade purity. 1,2-ethanedithiol (EDT) was purchased from Sigma Chemical Co. and used without further purification. All protected amino acids were of the L configuration unless otherwise indicated and were obtained from Bachem.

In solid phase synthesis methods, the reactive side chain groups of the various amino acid moieties are typically protected with suitable protecting groups which will prevent a chemical reaction from occurring at that site until the protecting group is ultimately removed. While specific protecting groups are disclosed in regard to the solid phase synthesis aspect, it should be noted that each amino acid can be protected by any protective groups conventionally used for the respective amino acids in solution phase synthesis. Among such protecting groups there are included for example conventional protecting groups for carboxyl groups selected from esters such as aryl esters, particularly phenyl or phenyl substituted with lower alkyl, halo, nitro, thio or lower alkyl (1–7 carbon atoms) thio. All α-amino groups were blocked with t-butyloxycarbonyl (Boc) functions. Side chain groups were substituted as follows: Asp, Ser, Thr with benzyl; Trp with formyl and Tyr with 2,6-dichlorobenzyl; Aeg with the benzyloxycarbonyl group. Purity of these compounds was confirmed by thin layer chromatography (TLC) and optical rotation. The benzlhydrylamine (BHA) resin was a copolymer of styrene −1% divinylbenzene in bead form (200–400 mesh) obtained from Beckman Instruments. Total nitrogen content was 0.654 meq/g.

The following instrumentation was utilized. Thin layer chromatography (TLC) was performed on glass backed precoated silica gel 60 F254 Plates (Merck) using appropriate solvent systems. Detection of spots was by UV fluorescence quenching (254 nm absorption), iodine staining, or ninhydrin spray (for primary and secondary amines).

For amino acid analyses, peptides were hydrolyzed in 6N HCl containing phenol at 115° C. for 24 hours in evacuated Reacti-Therm hydrolysis tubes. Analyses were Performed on a Beckman 121M amino acid analyzer.

High performance liquid chromatography (HPLC) was conducted on an LDC apparatus consisting of a Constametric I pump, a Constametric III Pump, a Gradient Master solvent programmer and mixer, and a Spectromonitor III variable wavelength UV detector. Analytical HPLC chromatography was performed on reversed phase with Waters Micro Bondapack $C_{18}$ columns (0.4×25)cm. Preparative HPLC separations were run on (2.5×50)cm Partisil M20 10/50 ODS-3 column, or (2.3×30)cm micro Bondapack $C_{18}$ column; in both cases, a pre-column of Whatman Co:Pell ODS pellicular packing was used.

The peptides were assembled in a stepwise manner on a solid support using a Vega 250 peptide synthesizer. The chemistry module was controlled by a Model 300 Microprocessor from Vega Biochemicals with manual operations at step 16 and 20.

Boc-Phe was coupled to the BHA resin (10 g) using Boc-Phe (4.24 g, 16 mmol) and DCC (1.66 g, 16 mmol) at 0° C. loading was determined by amino acid analysis to be 0.20 mmol/g resin. Any unreacted amino groups were capped by treating with 6 equivalents each of acetic anhydride and pyridine.

Boc-N-methyl-Phe was coupled to the benzylhydrylamine resin (5 g) using Boc-N-methyl-phe (5. g, 17. g mmol) and DCC (1.8 g 9 mmol) at 0° C., loaded was determined by amino acid analysis to be 0.20 mmol/g resin. Any unreacted amino groups were capped by treating with 6 equivalents each of acetic anhydride and pyridine.

The initial synthesis was started with resin and portions of peptide resin were removed at various points for separate analog preparation. The protocol for a typical synthetic cycle was as follows:

| Step | Reagent | Time |
|---|---|---|
| 1 | 1% EDT/CH$_2$Cl$_2$ | 1 × 30 sec |
| 2 | 50% TFA/CH$_2$Cl$_2$ w/1% EDT | 1 × 1 min |
| 3 | Repeat Step 1 | |
| 4 | 50% TFA/CH$_2$Cl$_2$ w/1% EDT | 1 × 15 min |
| 5 | CH$_2$Cl$_2$ | 1 × 30 sec |
| 6 | 2-Propanol | 1 × 30 sec |
| 7–8 | Repeat steps 5 & 6 | |
| 9 | CH$_2$Cl$_2$ | 2 × 30 sec |
| 10 | 8% DIPEA | 2 × 2 min |
| 11–15 | Repeat step 5–9 | |
| 16 | 5 equiv. Boc-AA anhydride | 1 × 30 min |
| 17 | 1% DIPEA | 1 × 5 min |
| 18–19 | Repeat steps 6 & 9 | |
| 20–21 | Repeat steps 16 & 17 if Kaiser test is positive | |
| 22 | 2-Propanol | 1 × 30 sec |
| 23–24 | Repeat steps 5 & 6 | |
| 25 | CH$_2$Cl$_2$ | 1 × 30 sec |
| 26 | DMF | 2 × 30 sec |
| 27 | CH$_2$Cl$_2$ | 3 × 30 sec |

Solvents for all washings and couplings were measured to volumes of 10–20 ml/g resin. Couplings were performed as the symmetrical anhydrides of the Boc-amino acids. They were performed in CH$_2$Cl$_2$ at 0° C. in 15 min. using 10 equivalents of Boc-amino acid and 5 equivalents of DCC.

Coupling reactions were monitored by the Kaiser ninhydrin test to determine whether coupling was complete after step 19. Kaiser, E. et al., *Anal. Biochem.*, 34. 595–598 (1970). Total cycle times ranged from 54–160 minutes per residue.

The fully assembled peptide-resins were dried under high vacuum overnight. Deblocking and cleavage conditions were the modified procedures of Tam et al. *Tetrahedron Letters*, 23, 4425,4438 (1982) and were optimized for CCK-8 analogs generally. The peptide-resin was treated in a teflon HF apparatus (Peninsula) with HF, dimethylsulfide and p-cresol (5:13:2) for 1 h at 0° C., after evaporation to a low volume fresh anhydrous HF was distilled into the reaction vessel (18 ml) for a second treatment for 1.5 h at 0° C. After thorough evaporation, the dry resin was washed with 3 volumes each of Et$_2$O and EtOAc, then triturated with 4 < 15 ml of 30% acetic acid and filtered. Lyophilization of the aqueous filtrate yielded the crude peptide.

Preparative purification were carried out directly on the crude unsulfated peptide by HPLC on a (2.3 × 30)cm micro Bondapack C$_{18}$ or (2.5–50)cm Whatman ODS-3 column. The peptides were applied in a minimum volume of 50% AcOH. and eluted with a slow gradient (4 hr) of 5–65%, 0.022% TFA/CH$_3$CN, at a flow rate of 8.0 ml/min. Fractions were collected at 3 minute intervals and cuts were made after inspection by analytical HPLC. Fractions, judged to be greater then 97% pure, were pooled and lyophilized.

Purity of the individual unsulfated peptides was checked by HPLC and determined to be 99% in all cases. Amino acid analyses of the individual peptides were performed and the expected values were obtained in each case. U.V., I.R., and M.S. were also performed on the analogs confirming the chemical integrity of the peptides.

Sulfation Procedure

The sulfate-ester containing peptides were prepared by double sulfation of the phenolic (tyrosine) and hydroxy (serine, threonine, or hydroxyproline) groups using pyridine Acetyl sulfuric acid reagent. As a typical sulfation was carried out as follows: 60–240 mg of pyridinum acetyl sulfate (PAS) was dissolved in 5% ml of pyridine and mixed at 60° C. for 10 minutes. N-acetyl-CCK-8 analog (10 mg) is dissolved in 5 ml of pyridine to which the PAS reagent is added. After heating and mixing for 45–60 min. at 60° C., it is neutralized with 2 volumes 0.05M ammonium bicarbonate lyophilized and purified by HPLC.

The sulfated peptides were purified by preparative reverse phase HPLC on a C$_{18}$–10μ (ES Industries) (1.25×30) cm column using a 2 hours gradient (10–40%) of acetonitrile in 0 05M ammonium bicarbonate with a flow rate of 5 ml/min and detection of 240 nm. Fractions pooling and peptide purity were determined by analytical HPLC using a Bondapack C$_{18}$, 10 micron Waters column (0.30×30) cm. and an acetonitrile in ammonium bicarbonate gradient with a flow of 2 ml and detection at 215 nm.

The purity of the sulfated peptides were determined by analytical HPLC, amino acid analysis, UV, IR, MS and NMR.

Deformylation Procedure

The formyl group was cleaved from the N$^{in}$-formyl-tryptophan containing CCK derivatives of the invention by adding 1 ml of 0.1N NH$_4$OH (pH 10.5) to 1 mg of peptide for 1 to 4 hours at room temperature followed by lyophilization.

The following examples illustrate in detail the preparation of the appetite suppressant peptides of the invention utilizing the procedures described above. In the examples described below, unless otherwise stated, the peptides were characterized and the purity was determined using amino acid analysis, analytical HPLC, U.V., I.R. and M.S.

EXAMPLE 1

Preparation of
Ac-Tyr(SO$_3$H)-Met-Gly-Trp(For)-Met-Thr(SO$_3$H)-N-methyl-Phe-NH$_2$

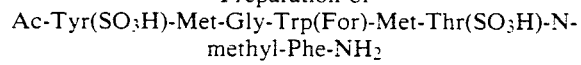

Boc-N-methyl-Phe (5 g 17.8 mmol) was dissolved in a mixture of 50 ml methylene chloride and 50 ml of dimethylformamide chilled to 0° C. and with stirring (1.8 g, 9 mmol) dicyclohexylcarbodiimide was added and the mixture was stirred for 60 minutes at 0° C.

Separately 5 g of benzylhydrylamine copolysterene 1% divinylbenzene cross—linked resin (0.56 mmole N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum.

Amino acid analysis showed the resin to contain 0.20 mmoles of N-methylphenylalanine per gram of resin. Unreacted amino groups were capped by shaking the resin with 5 ml of acetic anhydride and 5 ml diisopropylethylamine in methylene chloride for 60 minutes. The resin was filtered and washed with methylene chloride, isopropanol, dimethylformamide and methylene chloride. 4.8 g (0.96 mmole) of Boc-N-methylphenylalanine resin was subjected to sequential solid phase synthesis using the procedure described above. All couplings were performed using the symmetrical anhydrides of Boc-amino acids as described. At step 16 and 20 the activated amino acids were added with the corresponding reaction times as follows: six individual cycles were performed with Boc-O-benzyl-threonine (1.5 g, 5 mmole, 60 min, 1.5 g, 5 mmole, 60 min). Boc-methionine (1.25 g, 5 mmole, 30 min. 1.25 g 5 mmole. 30 min), Boc-$N^{in}$-formyl-tryptophan (1.7 g, 5 mmole, 30 min., 1.70 g. 5 mmole, 30 min), Boc-glycine (900 mg, 5 mmole. 30 min., 900 mg. 5 mmole, 30 min). Boc-methionine (1.25 g. 5 mmole 30 min, 1.25 g, 5 mmole, 30 min) and Boc-2-6-dichlorobenzyl-tyrosine (2.2 g, 5 mmole, 30 min, 2.2 g, 5 mmole, 30 min.).

Deprotection of the Boc-protecting group and acetylation of the resin with 20 ml acetic anhydride, 20 ml of pyridine in methylene chloride for 60 min. yielded 5.3 g of the acetylated-heptapeptide resin.

5.3 g of the resin was cleaved by treatment with 12 ml of HF containing dimethylsulfide (31 ml) and p-creosol (4.6 ml) for 1 hour at 0° C. After evaporation to a low volume, fresh anhydrous HF (42 mL) was distilled into the reaction vessel for a second treatment for 2 h at 0° C. After thorough evaporation, the resin was washed with 2 volumes of ethylacetate, then triturated with 4×15 mL of 30% acetic acid and filtered, lyophilized to yield 400 mg of crude peptide.

140 mg of the crude peptide was purified by preparative HPLC on a (2.5×50)cm partisil M 20 10/50 ODS 3 column. The peptide was eluted with a linear gradient of 5 to 65%, 0.022% TFA/CH$_3$CN at a flow rate of 8 ml/min., detection was at 280 nm. The main peak was collected and lyophilized to yield 55 mg (16.1%) of unsulfated analog. This material was homogeneous by HPLC and gave correct amino acid analysis.

To 60 mg of pyridinum acetyl sulfate (PAS) was added 10 ml of dry distilled pyridine. The resulting mixture was heated at 60° C., with stirring for 10 min. The solution was allowed to cool and 10 mg of Ac-Tyr-Met-Gly-Trp(For)-Met-Thr-N-methyl-Phe-NH$_2$ dissolved in 10 ml of pyridine was added to the solution and the reaction mixture was stirred for 1 hour at 60° C. Thereafter, the reaction mixture was neutralized with 2 volumes of ammonium bicarbonate, and lyophilized. Purification was achieved by preparative reverse phase HPLC on an ES-Industries C$_{18}$-10μ column (1.25×30)cm in using a linear gradient of 10-40% of 0.05M NH$_4$HCO$_3$/CH$_3$CN in 120 min with a flow rate of 5 ml/min and detection at 240 nm. The yield was 5 mg (43%) of Ac-Tyr-(SO$_3$H)-Met-Gly-Trp(For)-Met-Thr(SO$_3$H)-N-methyl-Phe-NH$_2$.

Amino Acid Analysis: Thr 0.91(1). Gly 1.00(1), Met 2.01(2), Tyr 1.00(1). Trp 1.03(1), N-methyl-Phe n.d.

Emp. Form: C$_{49}$H$_{63}$N$_9$O$_{17}$S$_4$; MW 1178.33

EXAMPLE 2

Preparation of
Ac-Tyr(SO$_3$H)-Met-Gly-Trp-Met-Thr(SO$_3$H)-N-methyl-Phe-NH$_2$ 2 mg of Ac-Tyr(SO$_3$H)-Met-Gly-Trp(For)-Met-Thr(SO$_3$H)-N-methyl-Phe-NH$_2$ was dissolved in 2.0 ml of 0.1N NH$_4$OH (pH 10.5) and allowed to stand for 1 hour at room temperature. The solution was then lyophilized to yield 1.7 mg (90%) of Ac-Tyr(SO$_3$H)-Met-Gly-Trp-Met-Thr(SO$_3$H)-N-methyl-Phe-NH$_2$.

Amino Acid Analysis: Thr 0.81 (1); Gly 1.02(1); Met 1.97(2); Tyr 1.00(1); Trp 1.03; N-methyl-Phe n.d.

Emp. Form: C$_{48}$H$_{63}$N$_9$O$_{16}$S$_4$; MW 1150.17.

EXAMPLE 3

Preparation of
Ac-Tyr-(SO$_3$H)-Nle-(D)Ala-Trp(For)-Met-Thr(SO$_3$H)-N-methyl-Phe-NH$_2$ 4.6 g (0.9 mmole) of Boc-N-methylphenylalanine resin which was obtained in the same way as in Example 1 was subjected to sequential solid phase synthesis using the same procedure as in Example 1. All couplings were performed using the symmetrical anhydrides of Boc-amino acids as described before. At step 16 and 20 the activated amino acids were added with the corresponding reactions times as follows: six individual cycles were Performed with Boc-0-benzyl-threonine(1.5 g, 5 mmole, 60 min. 1.5 g, 5 mmole, 60 min), Boc-methionine (1.25 g, 5 mmole. 30 min, 1.25 g, 5 mmole, 30 min), Boc-$N^{in}$-formyltryptophan (1.7 g. 5 mmole. 30 min. 1.7 g, 5 mmol. 30 min), Boc-(D)-alanine (950 mg, 5 mmole, 30 min), (960 mg, 5 mmole, 30 min.). Boc-Norleucine (1.15 g, 5 mmole, 60 min), (1.15 g, 5 mmole, 60 min.) and Boc-2,6-Dichlorobenzyl-tyrosine (2.2 g. 5 mmole, 30 min, 2.2 g, 5 mmole, 30 min).

Deprotection of the Boc-Protecting group and acetylation of the resin as in example 1 yield 5.2 g of the acetylatedheptapeptidyl resin. The resin was cleaved by treatment with HF containing dimethylsulfide and p-cresol using the procedure of Example 1. The resin was washed with Et$_2$O and EtOAc then triturated with 4×15 ml of 30% acetic acid, filtered and lyophilized to yield 80 mg of crude peptide.

80 mg of the crude peptide was Purified by preparative HPLC on a (2.3×30) cm micro Bondapack C$_{18}$ column. The peptide was eluted with a linear gradient (4 h) of 5% to 65%, 0.022% TFA/CH$_3$CN at a flow rate of 8 ml/min, detection was at 280 nm. The main peak was collected and lyophilized to yield 50 mg (5.36%) of the unsulfated CCK-8 analog. This material was homogeneous by HPLC, and gave the correct amino acid analysis.

10 mg of Ac-Tyr-Nle-(D)Ala-Trp(For)-Met-Thr-N-methyl-Phe-NH$_2$ were dissolved in 10 ml of pyridine and added to a solution of 240 mg of pyridinum acetyl sulfate (PAS) in 20 ml of pyridine prepared in the same manner as described in Example 1. The re... n mixture was stirred for 1 h at 60° C., then neutr... d with 2 volumes of ammonium bicarbonate, and l phified. Purification was achieved by preparative HPLC using the same condition as described in Example 1. The yield was 8 mg (70%) of Ac-Tyr(SO$_3$H)-Nle-(D)Ala-Trp(For)-Thr(SO$_3$H)-N-methyl-Phe-NH$_2$.

Amino Acid Analysis: Thr 0.95 (1); Ala 1.00(1), Met 0.98(1). Nle 0.98(1), Tyr 0.98(1), Trp 1.00(1), N-methyl-Phe n.d.

Emp. Form: C$_{51}$H$_{62}$N$_9$O$_{12}$S$_3$; MW 1174.32.

EXAMPLE 4

Preparation of
Ac-Tyr(SO$_3$H)-Nle-(D)Ala-Trp-Met-Thr(SO$_3$H)-n-Methyl-Phe-NH$_2$ The peptide of Example 3, Ac-Tyr(SO$_3$H)-Nle-(D)Ala-Trp-(For)-Met-Thr($O_3$H)-N-methyl-Phe-NH$_2$, (2 mg), was dissolved in 2 ml of 0.1N NH$_4$OH (PH 10.5) and allowed to stand for 4 hours at room temperature. The solution was then lyophilized to yield 1.8 mg (93%) of Ac-Tyr-(SO$_3$H)-Nle-(D)-Ala-Trp-Met-Thr(SO$_3$H)-N-methyl-Phe-NH$_2$. Amino Acid Analysis: Thr 0.92(1), Ala 1.04(1), Met 0.98(1), Nle 1.00(1), Tyr 0.99(1) Trp 0.80 (1), N-methyl-Phe n.d.

EXAMPLE 5

Preparation of
Ac-Tyr(SO$_3$H)-Met-Ala-Trp(For)-Met-Thr(SO$_3$H)-N-methyl-Phe-NH$_2$ 2.4 g (0.384 mmole) of Boc-N-methyl-Phenylalanine resin which was obtained in the same way as in Example 1 was subjected to sequential solid phase synthesis using the same protocol as in Example 1. All coupling were performed using the symmetrical anhydrides of Boc-amino-acids as described before. At step 16 and 20 the activated amino acids were added with the corresponding reactions times as follows: six individual cycles were performed with Boc-O-benzyl-threonine (1.5 g 5 mmole, 60 min, 1.5 g 5 mmole. 30 min), Boc-methionine (1.25 g, 5 mmole, 30 min., 1.25 g, 5 mmole, 30 min.), Boc N$^{in}$formyl-tryptophan (1.7 g, 5 mmole, 30 min, 1.7 g 5 mmole, 30 min) Boc-alanine (0.95 g, 5 mmole, 30 min, 1.25 g, 5 mmole, 30 min). and Boc-methionine (1.25 g, 5 mmole. 30 min, 1.25 g. 5 mmole, 30 min). Boc-2,6-dichlorobenzyl-tyrosine (2.2 g, 5 mmole, 30 min, 2.2 g, 5 mmole, 30 min).

Deprotection of the Boc-protecting group and acetylation of the resin as in Example 1 yielded 3.0 g of the acetylated-heptapeptide resin. The resin was cleaved by treatment with HF containing dimethylsulfide and p-creosol as described in Example 1. The resin was washed with ethylacetate, triturated with 30% acetic acid (4×15 ml), filtered and lyophilized to yield 100 g of crude peptide.

100 mg of the crude peptide was purified by preparative HPLC on a (2.5×50) cm. Partisil M 20 10/50 ODS-3 column. The peptide was eluted with a linear gradient of 5 to 65% 0.022% TFA/CH$_3$CN at a flow rate of 8 ml/min; detection was at 280 nm. The main peak was collected and lyophilized to yield 25 mg (6.6%) of unsulfated analog. This material was homogeneous by HPLC and gave the correct amino acid analysis.

12 mg of Ac-Tyr-Met-Ala-Trp(For)-Met-Thr-N-methyl-Phe-NH$_2$ was dissolved in 5 mL of pyridine and added to a solution of 170 mg pyridine-acetyl-sulfate (PAS) in 14 ml of pyridine in the same manner as described in Example 1. The reaction manner as described in Example 1. The reaction mixture was stirred for 1 hours at 60° C., then neutralized with 2 volumes of ammonium bicarbonate and lyophilized. Purification was achieved by preparative HPLC using the same condition as described in Example 1.

The yield was 9.8 mg (70%) of Ac-Tyr(SO$_3$H)-Met-Ala-Trp(For)-Met-Thr(SO$_3$H)-N-methyl-Phe-NH$_2$.

Amino Acid Analysis. Thr 0.98(1), Ala 1.1(1), Met 2.00(2), Tyr 1.14(1), N-methyl-Phe n.d., Trp. n.d.
Emp. form C$_{50}$H$_{65}$N$_5$O$_{12}$S$_4$ N.W. 1137.14.

Example 6

Preparation of
Ac-Tyr(SO$_3$H)-Met-Ala-Trp-Met-Thr(SO$_3$H)-N-methyl-Phe-NH$_2$ 2 mg of Ac-Tyr(SO$_3$H)-Met-Ala-Trp(For)-Met-Thr(SO$_3$H)-N-Methyl-Phe-NH$_2$ were dissolved in 2 mL of 0.1N NH$_4$OH (pH 10.5) and allowed to stand for 4 hours at room temperature. The solution was then lyophilized to yield 1.9 mg (95%) of Ac-Tyr-(SO$_3$H)-Met-Ala-Trp-Met-Thr(SO$_3$H)-N-methyl-Phe-NH$_2$.

The peptide was characterized by amino acid analysis U.V., I.R. and amino acid analysis.

Amino acid analysis, Thr 0.81(1), Ala 1.0(1), Met 1.96(2), Tyr 0.97(1), Trp n.d. and N-methyl Phe n.d.
Emp. Form: C$_{51}$H$_{65}$N$_9$O$_{10}$S$_4$; M.W. 1164.34.

EXAMPLE 7

Preparation of
Ac-Aeg-Tyr(SO$_3$H)-Met-Gly-Trp(For)-Met-Thr(SO$_3$H)-N-methyl-Phe-NH$_2$ Boc N-methylphenylalanine resin 4.4 g (0.9 mmole) which was obtained in the same way as in Example 1 was subjected to sequential solid phase synthesis using the same protocol as in Example 1. All couplings were performed using the symmetrical anhydrides of Boc-amino acids as previously described. At step 6 and 20, the activated amino acids were added with the corresponding reactions times as follows: seven individual cycles were performed with Boc 0-benzyl-threonine (1.5 g, 5 mmole. 60 min, 1.5 g, 5 mmole 60 min), Boc-methionine (1.25·g 5 mmole 30 min 1.25 g, 5 mmole. 30 min). Boc-N$^{in}$-formyl-tryptophan (1.7 g, 5 mmole, 30 min, 1.7 g 5 mmole, 30 min). Boc-glycine (900 mg, 5 mmole, 30 min, 900 mg 5 mmole, 30 min). Boc-methionine (1.25 g, 5 mmole, 30 min 1.25 g, 5 mmole, 30 min). Boc-2-6-dichlorobenzyl-tyrosine (2.2 g, 5 mmole. 30 min, 2.2 g, 5 mmole, 30 min). Boc-Aeg(Z)-OH (3.5 g, 5 mmol. 60 min, 3.5 g. 5 mmole. 30 min).

Deprotection of the Boc-protecting group and acetylation of the resin as in example 1 yielded 5.6 g of the acetylated octapeptidyl resin. The resin was cleaved by treatment with HF containing dimethylsulfide and p-cresol using the modified procedure of Tam et al. and as described in detail in Example 1. The resin was washed with ethylacetate then triturated with 4×15 mL of 30% acetic acid filtered and lyophilized to yield 582 mg of crude peptide. 75 mg of the crude peptide was purified by preparative HPLC on a (2.5×50) cm. Partisil M10/50 ODS-3 column. The peptide was eluted with a linear gradient of 5 to 65% 0.022% TFA/CH$_3$CN at a flow rate of 3 mL/ml. Detection at 280 nm. The main peak was collected and lyophilized to yield 8 mg (6.2%) of unsulfated analog. this material was homogeneous by HPLC and gave the correct amino acid analysis.

8 mg of Ac-Aeg-Try-Met-Gly-Trp(For)-Met-Thr-N-methyl-Phe-NH$_2$ was dissolved in 5 ml of pyridine and added to a solution of 180 mg of pyridine-acetyl-sulfate (PAS) in 15 ml of pyridine in the same manner as described in Example 1. The reaction mixture was stirred for 1 hour at 60° C., then neutralized with 2 volumes of ammonium bicarbonate and lyophilized. Purification was achieved by preparative HPLC using the same conditions as described in Example 1. The yield was 45 mg (45%) of Ac-Aeg-Tyr(SO$_3$H)-Met-Gly-Trp(For)-Met-Thr(SO$_3$H)-N-methyl-Phe-NH$_2$.

Amino Acid Analysis: Thr 1.00 (1); Gly 1.14(1) Met 2.13(2); Tyr 1.10(1) Trp 0.90(1); Aeg 1.00(1), N-methyl-Phe n.d.

Emp. From C$_{53}$H$_{74}$N$_{11}$O$_{18}$S$_3$; MW 1278.37

Unlike native CCK-8, which binds to receptor sites in the pancreas and brain, the peptides of the invention bind primarily to receptor sites in the pancreas. Further, the peptides of the invention are more resistant to degradation by various gastrointestinal peptidase enzymes than is CCK-8; as a result, the peptides of the invention, and especially those of Formula Ia, are longer acting than CCK-8.

The following examples illustrate the in vitro and in vivo biological activities of the Peptides of formula I, II and III.

Example 8 illustrates the specific binding of the peptides of the invention to receptors in homogenized preparations of rat pancreatic cells and bovine striata compared to the binding of native CCK-8 using $^3$H-CCK-8-(SO$_3$H) as a radioligand. Unlike native CCK-8, which binds to receptor sites in the pancreas and brain, the peptides of the invention bind selectively to receptor sites in the pancreas. This strategy was utilized to minimize central nervous system side effects by identifying peptides with peripheral receptor selectivity. Thus, the peptides of the invention, which are inactive in binding with high affinity to the central receptor, are unlikely to elicit behavioral side effects.

EXAMPLE 8

In Vitro Receptor Binding Assay

Frozen bovine striatum (approx. 5 g) and fresh rat pancreas (approx. 5 g) cleaned of fat and extraneous tissue were homogenized in HEPES buffer #1 (10 mM HEPES+130 mM NaCl+5 mM MgCl$_2$. pH 7.4) using 35 parts buffer per 1 part tissue on a wet weight/volume basis (approx. 175 ml). The tissue was homogenized 2 x for approx. 15 sec. at 0° C. using a Polytron homogenizer at a setting of 6. The tissue was isolated by centrifugation at 48,000 x g for 10 min. at 0° C. The resulting tissue pellet was resuspended in HEPES buffer #2 (10 mM HEPES+130 mM NaCl+5 mM MgCl$_2$+1 mg/L phenylmethanesulfonyl fluoride (PMSF)+200 mg/L Bacitracin): 1 part striatal tissue (original wet weight) per 80 parts buffer and 1 part pancreas tissue (original wet weight) per 70 parts buffer.

Incubation was initiated by combining various concentrations of native CCK-8 or peptides of formula I, II and III with $^3$H-CCK-8-(SO$_3$H) (final conc.=0.15 nM) and tissue homogenate (striatum 0.26 mg protein in 2 ml final volume; pancreas 0.165 mg protein in 1 ml final volume). Samples were incubated for 30 min. at 25° C. and the incubation terminated by pouring the mixture onto a pre-wet Whatman GF/B filter on a Sandbeck Vacuum Filtration Manifold. The incubation tubes were washed with 2×3 ml of ice-cold HEPES Buffer #2 and the wash filtered through the GF/B filter. The filter was air dried for 10 min. and then placed in a scintillation vial with 12 ml of Beckman HP/b Ready-Solv scintillation cocktail. The vials were shaken for 2 hours and then counted using a Beckman Model 7800 liquid scintillation spectrometer. Non-specific binding was determined in the presence of 1 micromole native CCK-8 and subtracted from all samples to determine specific binding. The concentration of $^3$peptide necessary to inhibit 50% of total specific H-CCK-8-(SO$_3$H) binding (IC$_{50}$ value) was determined by log-probit analysis.

The results are summarized in Table 1.

EXAMPLE 9

Two-Meal Feeding Assay

Male Sprague-Dawley (CD) rats weighing 180-200 grams (Charles River Breeding Laboratories) were acclimated to a 12 h light/dark cycle (6 a.m. to 6 p.m.) in a room kept at 22° C. They were subsequently fasted for two days, weighed, placed in individual cages, and a four-day period of meal training was begun. During this time the rats were given ground laboratory chow (Purina Lab Chow) in jars for one hour from 9:00 a.m. until 10:00 a.m., the jars were removed from 10:00 a.m. to 12:00 p.m., and placed back in the cages from 12:00 until 1:00 p.m. Under this '1-2-1' meal feeding regime most rats learn to eat approximately as much per day during the two hours they have access to food as rats which have food ad libitum over the entire 24-hour day. On the fourth day, the rats were weighed again, and any which lost more than five grams body weight were excluded from the test. The animals were then distributed into experimental (n=5 to 6) and control groups (n=6-12). but not matched for body weight.

Peptides of the invention were suspended either in saline. if soluble, or in 1% gum arabic, if insoluble, at concentrations of 0 to 320 μg/ml/kg body weight and were administered intraperitonerally 15 min before the first meal on day 5 of meal feeding. The rats were then given their meals as they had been during the previous four days, and the food cups were weighed both before and after each meal to determine food consumption. Food intake was expressed as a mean and standard error of the mean in grams consumed or as a percent of control values for the various groups. The treated groups were compared to the control groups by t-test analysis. The results are summarized in Table 1.

EXAMPLE 10

Male rats were meal trained as described in Example 9. The peptide of Example 2 and CCK-8 were administered as in Example 9 over the dosage range shown in FIG. 1. As illustrated by FIG. 1, the peptide of Example 2 effectively reduced food intake during the first meal at a much lower dosage range than did CCK-8.

The following example illustrates the satiety inducing effect of the peptide of Example 2 when administered intranasally.

EXAMPLE 11

Male rats were meal trained as described in Example 9. The peptide of Example 2 was dissolved in saline and was administered to the rats intranasally. CCK-8, dissolved in saline was used as a control. The results are summarized in Table 2.

TABLE 2

| Treatment | Dose μg/kg | Food Intake 1st meal Grams consumed (%) | 2nd meal Grams consumed (%) |
|---|---|---|---|
| Saline | — | 7.4 ± 0.5 (100) | 5.6 ± 0.3 (100) |
| Peptide of Example 2 | 3 | 7.5 ± 0.8 (102) | 6.1 ± 0.3 (109) |
|  | 10 | 5.5 ± 0.6 (74)* | 6.3 ± 0.4 (112) |
|  | 30 | 5.8 ± 0.7 (78) | 4.3 ± 0.6 (76) |
|  | 100 | 3.4 ± 0.4 (46)*** | 4.6 ± 0.5 (82) |
| CCK-8 | 1000 | 4.9 ± 0.7 (66)* | 6.3 ± 05 (112) |
|  | 400 | Inactive | |

Values significantly different from their respective controls:
***p ≦ 0.001:
*p ≦ 0.05.

As illustrated by Example 12, the peptides of the invention are more resistant than is CCK-8 to degradation by enzymes which breakdown peptides.

EXAMPLE 12

Rat kidney metalloendopeptidase (0.01 μg) and 5 nmol of peptide were incubated in 2 μmol tris-HCl buffer (pH 7.6) and at 37° C. for varying periods of time. The degradation of the peptide was monitored by analytical HPLC on a 5 micron Adsorbosphere-ODS column with a 0-50% CH$_3$CN gradient in 0.1N potassium phosphate, pH 3.0, with UV detection at 210 nm. Rates are based on presumed production of Asp-Tyr(SO₃H)-Met-Gly for CCK-8 and the presumed production of Ac-Tyr(SO₃H)-Met-Gly for Example 2 and 3.

TABLE 3

Degradation of CCK-8 and Peptides of the Invention by Rat Kidney Metalloendopeptidase

| Peptide of Example | Time of Incubation (min) | % Degradation by Height | No. of Peaks |
|---|---|---|---|
| CCK-8 | 0 | 0 | |
| | 15 | 6.2 | |
| | 30 | 33.2 | |
| | 60 | 69.7 | 4 |
| 2 | 0 | 0 | |
| | 60 | 19.4 | |
| | 120 | 30.3 | |
| | 240 | 56.4 | 2* |
| 3 | 0 | 0 | |
| | 60 | 0 | |
| | 120 | 0 | |
| | 240 | 0 | 0 |

*Indicates one peak detected and one peak that co-eluted with substrate that was differentiated based on molar ratios following amino acid analysis.

EXAMPLE 13

Preparation of
A-Tyr(SO₃H)-Nle-Gly-Trp-Nle-Thr(SO₃H)-N-methyl-Phe-NH₂

Boc-N-methyl-Phe (5 g, 17.8 mmol) was dissolved in a mixture of 50 ml methylene chloride and 50 ml of dimethylformamide chilled to 0° C. and with stirring (1.8 g, 9 mmol) dicyclohexylcarbodiimide was added and the mixture was stirred for 60 minutes at 0° C.

Separately 5% of benzylhydrylamine-copolysterene 1%-divinylbenzene cross-linked resin (0.56 mmole N/g) was washed with 10% diisopropylethylamine in methylene chloride for 30 min, filtered and washed with methylene chloride, dimethylformamide, and methylene chloride. The chilled mixture above was added to the resin and stirred for 24 hours at room temperature. The resin was filtered, washed with methylene chloride, dimethylformamide, isopropanol, methylene chloride dimethylformamide, isopropanol, and methylene chloride, and dried under high vacuum.

Amino acid analysis showed the resin to contain 0.20 mmoles of N-methyl-phenylalanine per gram of resin. Unreacted amino groups were capped by shaking the resin with 5 ml of acetic anhydride and 5 ml diisopropylethylamine in methylene chloride for 60 minutes. The resin was filtered and washed with methylene chloride isopropanol, dimethylformamide and methylene chloride. Two grams (0.4 mmol) of Boc-N-methyl-phenylalanine resin was subjected to sequential solid phase synthesis using the same procedure as in Example 1. All couplings were performed using the symmetrical anhydrides of Boc amino acids as described. At step 16 and 20 the activated amino acids were added with the corresponding reaction times as follows: six individual cycles were performed with Boc-0-benzyl-threonine (610 mg, 2 mmole, 60 min., 610 mg, 2 mmole, 60 min.), Boc-norleucine (460 mg, 2 mmole, 30 min., 460 mg, 2 mmole, 30 min.), Boc-N$^{in}$-formyl-tryptophan (665 mg, 2 mmole, 30 min. 665 mg, 2 mmole, 30 min), Boc-glycine (350 mg, 2 mmole, 30 min., 350 mg, 2 mmole, 30 min.), Boc-norleucine (460 mg. 2 mmole, 30 min., 460 mg, 2 mmole, 30 min.) and Boc-2-6-dichlorobenzyl-tyrosine (880 mg, 2 mmole, 30 min, 880 mg, 2 mmole, 30 min.).

Deprotection of the Boc-protecting group and acetylation of the resin with 10 ml acetic anhydride, 10 ml of pyridine in methylene chloride for 60 min. yielded 2.93 g of the acetylated-heptapeptidyl resin.

2.93 g of the resin was cleaved by treatment with 6 ml of HF containing dimethylsulfide (20 ml), anisol (3 ml) and (1 ml) ethanedithiol for 1 hour at 0° C. After evaporation to a low volume fresh anhydrous HF (15 ml) was distilled into the reaction vessel for a second treatment for 1 hour at 0° C. After thorough evaporation the resin was washed with ethylacetate, then titurated with 4×15 mL of 50% acetic acid filtered and lyophilized to yield 480 mg of crude peptide. 85 mg of the crude peptide was purified by preparative HPLC on a (2.3×30) cm micro Bondapack C₁₈ column. The peptide was eluted with a linear gradient of 5 to 65%, 0.022% TFA/CH₃CN at a flow rate of 8 ml/min., detection was at 280 nm. The main peak was collected and lyophilized to yield 22 mg (31%) Ac-Tyr-Nle-Gly-Trp-Nle-Thr-N-methyl-Phe-NH₂. This material was homogenous by HPLC and gave the correct amino acid analysis.

To 60 mg of pyridium acetyl sulfate (PAS) was added 10 ml of dry distilled Pyridine. The resulting mixture was heated at 60° C. with stirring for 10 min. The solution was allowed to cool, and 10 mg of Ac-Tyr-Nle-Gly-Trp-Nle-N-methyl-Phe-NH₂ dissolved in 10 ml of pyridine was added to the solution and the reaction mixture was stirred for 1 hour at 60° C. Thereafter, the reaction mixture was neutralized with 2 volumes of ammonium bicarbonate and lyophilized. Purification was achieved by preparative reverse phrase HPLC on an ES Industries C₁₈-10 micron column (1.25×30) cm using a linear gradient of 10–40% of 0.05M NH₄HCO₃/CH₃CN in 120 min. with a flow rate of 5 ml/min and detection at 240 min. the yield was 8 mg (66%) of Ac-Tyr-(SO₃H)-Nle-Gly-Trp-Nle-Thr(SO₃H)-N-methyl-Phe-NH₂. This material was homageneous by HPLC and gave the following amino acid analysis: AsP 0.90 (1); Gly 1.00 (1); Nle 2.00; Tyr 1.00 (1); Trp 0.60 (1); N-methyl-Phe. n.d.

Emp. form. C₅₀H₆₇N₈O₁₆S₂ MW 1114. 5

EXAMPLE 14

Preparation of
Ac-Tyr(SO₃H)-Gly-Trp-Met-Thr(SO₃H)-N-methyl-Phe-NH₂

1.5 g (0.3 mmol) of Boc-N-methyl-phenylalanine resin which was obtained in the same way as in Example 1 was subjected to sequential solid phase synthesis using the same procedure as in Example 1. All couplings were performed using the symmetrical anydrides of Boc-amino acids as described before. At step 16 and 20 the activated amino acids were added with the corresponding reaction times as follows: five individual cycles were performed with Boc-O-benzyl-threonine (610 mg. 2 mmole. 60 min, 610 mg, 2 mmol. 60 min), Boc-methionine (500 mg. 2 mmole, 30 min. 500 mg. 2 mmole, 30 min), Boc-N$^{in}$-formyl tryptophan (665 mg, 2 mmole, 30 min. 665 mg, 2 mmole, 30 min). Boc-glycine (350 mg, 2 mmole. 30 min., 350 mg, 2 mmole, 30 min.), and Boc-2,6- dichlorobenzyl-tyrosine (880 mg, 2 mmole, 30 min. 880 mg, 2 mmole. 30 min). Deprotection of the Boc-protecting group and acetylation of the resin with 8 ml acetic anhydride, 8 ml pyridine in methylene chloride for 60 min yielded 1.65 g of the acetylated hexapeptide resin.

The resin was cleaved by treatment with HF containing dimethylsulfide,. anisol, and ethanedithiol using the same procedure as in example 1. The resin was washed with ether and ethylacetate then titrated with 30% acetic acid, filtered and lyophilized to yield 110 mg of crude peptide.

110 mg of this crude peptide was purified by preparative HPLC on a (2.3×30) cm micro Bondapack $C_{18}$ column. The peptide was eluted with a linear gradient of 5-65%, 0.022% TFA/$CH_3CN$ at a flow rate of 8 ml/min., detection was at 280 nm. The main peak was collected and lyophilized to yield 15 mg (11.6%) of Ac-Tyr-Gly-Trp-Met-Thr-N-methyl-Phe-$NH_2$ this material was homogenous by HPLC and gave the correct amino acid analysis.

15 mg of Ac-Tyr-Gly-Trp-Met-Thr-N-methyl-Phe-$NH_2$ were dissolved in 15 ml of pyridine and added to a solution of 240 mg of pyridium acetyl sulfate (PAS) in 20 ml of pyridine prepared in the same manner as described in Example 1. The reaction mixture was stirred for 1 h at 60° C. then neutralized with 2 volumes of ammonium bicarbonate, and lyophilized. Purifications was achieved by preparative HPLC using the same condition as described in Example 1. The yield was 11 mg (61%) of Ac-Tyr($SO_3H$)-Gly-Trp-Met-Thr($SO_3H$)-N-methyl-Phe-$NH_2$.

Amino acid analysis: Thr 0.86(1); Glu 1.00(1); Met 1.02(1); Tyr 1.01(1); Trp 0.72(1); N-methyl-Phe n.d.

Emp. form. $C_{43}H_{54}N_8O_{15}S_3$ MW. 1019.01

The peptides of Formula I are useful in a method for suppressing or reducing food intake in a mammal which method comprises administering to said mammal an effective food intake suppressing amount of a peptide of Formula I or a pharmaceutically acceptable salt thereof. The peptides of formula I may be administered either to mammals in a variety of dosage forms e.g., intravenously, intraperitoneally. sublingually, rectally, intranasally, buccally or transdermally.

The appetite suppressant compositions are not specifically limited in the mode of administration but can be given by a suitable method in accordance with the particular form of the composition. For example, injections are given intravenously, singly or admixed with an auxiliary solution of saline, etc. Suppositories are given to the rectum, while nasal preparations are administered through the nostril.

The pharmaceutical or veterinary compositions containing a peptide of the invention and/or salts thereof may be prepared in a conventional way and contain conventional carriers and/or diluents.

When formulated for injection, peptides of the invention and salts thereof are preferably presented as sterile powder to be reconstituted with water for injections or other suitable sterile vehicle shortly before administration. For example, for intravenous injections, sterile aqueous isotonic solutions may be used, preferably sodium chloride isotonic aqueous solution. The sterile powder is conveniently obtained by means of lyophilization; in that case the active ingredient is conveniently admixed with an inert carrier, such as lactose.

TABLE 1

| Peptides | (Ex. No.) | Bovine Striatum (nM) | Rat Pancreas (nM) | Dose microgm/Kg | Food Intake | |
|---|---|---|---|---|---|---|
| | | | | | 1st Meal % of Control | 2nd Meal % of Control |
| Asp—Tyr($SO_3H$)—Met—Gly—Trp—Met—Asp—Phe—$NH_2$ | CCK-8 | 1–3.2 | 1–4.6 | 32 | 27 ± 17*** | 149 ± 6*** |
| Ac—Tyr($SO_3H$)—Met—Gly—Trp(For)—Met—Thr($SO_3H$)—N—methyl—Phe—$NH_2$ | 1 | 1000 | 9.4 | 32 | 23 ± 13*** | 55 ± 10* |
| Ac—Tyr($SO_3H$)—Met—Gly—Trp—Met—Thr($SO_3H$)—N—methyl—Phe—$NH_2$ | 2 | 100–500 | 2.2 | 32 | 8 ± 1*** | 26 ± 4*** |
| Ac—Tyr($SO_3H$)—Nle—(D)Ala—Trp(For)—Met—Thr($SO_3H$)—N—methyl Phe—$NH_2$ | 3 | 100 | 100 | 32 | 34 ± 6*** | 164 ± 16** |
| Ac—Tyr($SO_3H$)—Nle—(D)Ala—Trp—Met—Thr($SO_3H$)—N—methyl Phe—$NH_2$ | 4 | 100 | 44 | 32 | 5 ± 5*** | 79 ± 13 |
| Ac—Tyr($SO_3H$)—Met—Ala—Trp(For)—Met—Thr($SO_3H$)—N—methyl—Phe—$NH_2$ | 5 | 4100 | 4200 | 32 | 70 ± 2** | 133 ± 9** |
| Ac—Tyr($SO_3H$)—Met—Ala—Trp—Met—Thr($SO_3H$)—N—methyl—Phe—$NH_2$ | 6 | 1750 | 100 | 32 | 14 ± 6*** | 114 ± 9 |
| Ac—Aeg—Tyr($SO_3H$)—Met—Gly—Trp(For)—Met—Thr($SO_3H$)—N—methyl—Phe—$NH_2$ | 7 | 1000 | 14.5 | 32 | 17 ± 9*** | 95 ± 16 |
| —Tyr($SO_3H$)—Nle—Gly—Trp—Nle—Thr($SO_3H$)—N—methyl—Phe—$NH_2$ | 13 | 245 | 0.14 | 32 | 21 ± 12*** | 52 ± 13** |
| | | | | 16 | 27 ± 17** | 45 ± 11** |
| | | | | 10 | 13 ± 1*** | 62 ± 8 |
| | | | | 3 | 23 ± 13*** | 59 ± 6 |
| | | | | 1 | 36 ± 4*** | 71 ± 13 |
| Ac—Tyr($SO_3H$)—Gly—Trp—Met—Thr($SO_3H$)—N—methyl—Phe—$NH_2$ | 14 | 1600 | 70 | 320 | 4 ± 5*** | 121 ± 3 |
| | | | | 32 | 36 ± 8*** | 141 ± 9** |
| | | | | 3 | 86 ± 16 | 120 ± 13 |

Values significantly different then their respective controls
***$p \leq 0.001$.
**$p \leq 0.01$.
*$p \leq 0.05$

What is claimed is:

1. A peptide of the formula

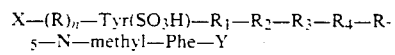

wherein

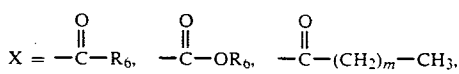

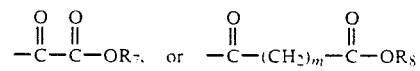

R = Asp or Aeg
$R_1$ = Met, Nle, Leu, Ile, or a bond
$R_2$ = Gly, Ala, D-Ala, or α-Ala
$R_3$ = Trp or Trp(For)
$R_4$ = Met, Nle, or Nva
$R_5$ = Thr($SO_3H$), Ser($SO_3H$), or Hyp($SO_3H$)
$R_6$ = H or $C_{1-3}$ alkyl
$R_7$ = H, $C_{1-3}$ alkyl, or $C_{1-3}$ haloalkyl $R_8$=H or $C_{1-3}$ alkyl
Y=$OR_8$ or $NR_9R_{10}$
$R_9$=H or $C_{1-3}$ alkyl
$R_{10}$=H or $C_{1-3}$ alkyl
n=0 or 1
m=1-14
or the pharmaceutically acceptable salt.

2. The peptide of claim 1 wherein X=Ac; R=Aeg and n=1; $R_1$=Met, Nle or a bond; $R_2$=Gly, D-Ala, or Ala; $R_3$=Trp or Trp(For); $R_4$=Met or Nle; $R_5$=Thr($SO_3H$) and Y=$NH_2$.

3. The peptide of claim 2 wherein R=Aeg and N=1; $R_1$=Met; $R_2$=Gly; $R_3$=Trp(For); $R_4$=Met; $R_5$=Thr($SO_3H$); and Y=$NH_2$; said peptide having the formula:

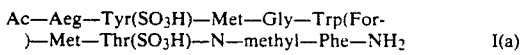

Ac—Aeg—Tyr($SO_3H$)—Met—Gly—Trp(For)—Met—Thr($SO_3H$)—N—methyl—Phe—$NH_2$    I(a)

4. The peptide of claim 1 wherein X=Ac; (R)n where n=0; $R_1$=Met, Nle; $R_2$=Gly, D-Ala, Ala; $R_3$=Trp, or Trp(For); $R_4$=Met or Nle; $R_5$=Thr($SO_3H$); and Y=$NH_2$.

5. The peptide of claim 4 wherein X=Ac; n=0; $R_1$=Met; $R_2$=Gly; $R_3$=Trp(For); $R_4$=Met; $R_5$=Thr($SO_3H$); and Y=$NH_2$ said peptide having the formula:

Ac—Tyr($SO_3H$)—Met—Gly—Trp(For)—Met—Thr($SO_3H$)—N—methyl—Phe—$NH_2$    I(b)

6. The peptide of claim 4 wherein $R_1$=Met; $R_2$=Gly; $R_3$=Trp; $R_4$=Met; $R_5$=Thr($SO_3H$) and Y=$NH_2$ said peptide having the formula:

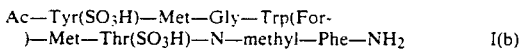

Ac—Tyr($SO_3H$)—Met—Gly—Trp—Met—Thr($SO_3H$)—N—methyl—Phe—$NH_2$    I(c)

7. The peptide of claim 4 wherein X=Ac; n=0; $R_1$=Nle; $R_2$=D-Ala; $R_3$=Trp(For); $R_4$=Met; $R_5$=Thr($SO_3H$); and Y=$NH_2$ said peptide having the formula:

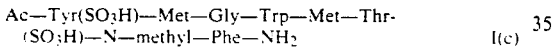

Ac—Tyr($SO_3H$)—Nle—(D)Ala—Trp(For)—Met—Thr($SO_3H$)—N—methyl—Phe—$NH_2$    I(d)

8. The peptide of claim 4 wherein X=Acetyl; n=0; $R_1$=Nle; $R_2$=D-Ala; $R_3$=Trp; $R_4$=Met; $R_5$=Thr($SO_3H$); and Y=$NH_2$ said peptide having the formula:

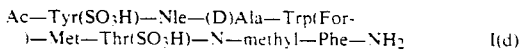

Ac—Tyr($SO_3H$)—Nle—(D)Ala—Trp—Met—Thr($SO_3H$)—N—methyl—Phe—$NH_2$    I(e)

9. The peptide of claim 4 wherein X-Ac; $R_1$=Met; $R_2$=Ala; $R_3$=Trp(For); $R_4$=Met; $R_5$=Thr($SO_3H$); and Y=$NH_2$ said peptide having the formula:

Ac—Tyr($SO_3H$)—Met—Ala—Trp(For)—Met—Thr($SO_3H$)—N—methyl—Phe—$NH_2$    I(f)

10. The peptide of claim 4 wherein X=Ac; n=0; $R_1$=Met; $R_2$=Ala; $R_3$=Trp; $R_4$=Met; $R_5$=Thr($SO_3H$); and Y=$NH_2$ said peptide having the formula:

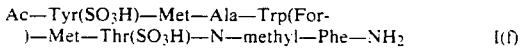

Ac—Tyr($SO_3H$)—Met—Ala—Trp—Met—Thr($SO_3H$)—N—methyl—Phe—$NH_2$    I(g)

11. The peptide of claim 4 wherein X=Ac; n=0; $R_1$=Nle; $R_2$=Gly; $R_3$=Trp; $R_4$=Nle; $R_5$=Thr($SO_3H$); and Y=$NH_2$ said peptide having the formula:

Ac—Tyr($SO_3H$)—Nle—Gly—Trp—Nle—Thr($SO_3H$)—N—methyl—Phe—$NH_2$    I(h)

12. The peptide of claim 4 wherein X=Ac; n=0; $R_1$=a bond; $R_2$=Gly; $R_3$=Trp; $R_4$=Met; $R_5$=Thr($SO_3H$); and and Y=$NH_2$ said peptide having the formula:

Ac—Tyr($SO_3H$)—Gly—Trp—Met—Thr($SO_3H$)—N—methyl—Phe—$NH_2$    I(i)

13. A method for suppressing food intake in mammals comprising administering to said mammal an effective food intake suppressing amount of a peptide of the formula:

X—(R)$_n$—Tyr($SO_3H$)—$R_1$—$R_2$—$R_3$—$R_4$—$R_5$—N—methyl—Phe—Y wherein

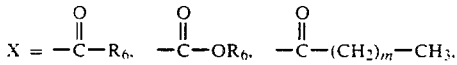
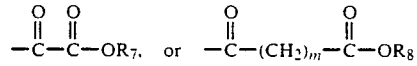

$$X = -\overset{O}{\underset{\|}{C}}-R_6, \quad -\overset{O}{\underset{\|}{C}}-OR_6, \quad -\overset{O}{\underset{\|}{C}}-(CH_2)_m-CH_3,$$

$$-\overset{O}{\underset{\|}{C}}-\overset{O}{\underset{\|}{C}}-OR_7, \text{ or } -\overset{O}{\underset{\|}{C}}-(CH_2)_m-\overset{O}{\underset{\|}{C}}-OR_8$$

R=Asp or Aeg
$R_1$=Met, Nle, Leu, Ile, or a bond
$R_2$=Gly, Ala, D-Ala, or β-Ala
$R_3$=Trp or Trp(For)
$R_4$=Met, Nle, or Nva
$R_5$=Thr($SO_3H$), Ser($SO_3H$), or Hyp($SO_3H$)
$R_6$=H or $C_{1-3}$ alkyl
$R_7$=H, $C_{1-3}$ alkyl, or $C_{1-3}$ haloalkyl
$R_8$=H or $C_{1-3}$ alkyl
Y=$OR_8$ or $NR_9R_{10}$
$R_9$=H or $C_{1-3}$ alkyl
$R_{10}$=H or $C_{1-3}$ alkyl
n=0 or 1
m=1-4
or the pharmaceutically acceptable salt.

14. The method of claim 13 wherein the peptide has the formula:

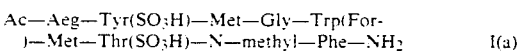

Ac—Aeg—Tyr($SO_3H$)—Met—Gly—Trp(For)—Met—Thr($SO_3H$)—N—methyl—Phe—$NH_2$    I(a)

15. The method of claim 13 wherein the peptide is of the formula

Ac—Tyr($SO_3H$)—Met—Gly—Trp(For)—Met—Thr($SO_3H$)—N—methyl—Phe—$NH_2$    I(b)

16. The method of claim 13 wherein the peptide has the formula:

Ac—Tyr($SO_3H$)—Met—Gly—Trp—Met—Thr($SO_3H$)—N—methyl—Phe—$NH_2$    I(c)

17. The method of claim 13 wherein the peptide has the formula:

Ac—Tyr($SO_3H$)—Nle—(D)Ala—Trp(For)—Met—Thr($SO_3H$)—N—methyl—Phe—$NH_2$    I(d)

18. The method of claim 13 wherein the peptide has the formula:

Ac—Tyr(SO₃H)—Nle—(D)Ala—Trp—Met—Thr(SO₃H)—N—methyl—Phe—NH₂     I(e)

19. The method of claim 13 wherein the peptide has the formula:

Ac—Tyr(SO₃H)—Met—Ala—Trp(For)—Met—Thr(SO₃H)—N—methyl—Phe—NH₂     I(f)

20. The method of claim 13 wherein the peptide has the formula:

Ac—Tyr(SO₃H)—Met—Ala—Trp—Met—Thr(SO₃H)—N—methyl—Phe—NH₂     I(g)

21. The method of claim 13 wherein the peptide has the formula:

Ac—Tyr(SO₃H)—Nle—Gly—Trp—Nle—Thr(SO₃H)—N—methyl—Phe—NH₂     I(h)

22. The method of claim 13 wherein the peptide has the formula:

Ac—Tyr(SO₃H)—Gly—Trp—Met—Thr(SO₃H)—N—methyl—Phe—NH₂     I(i)

* * * * *

UNITED STATES PATENT AND TRADEMARK OFFICE
CERTIFICATE OF CORRECTION

PATENT NO. : 5,013,722

DATED : May 7, 1991

INVENTOR(S) : Waleed Danho, et al.

It is certified that error appears in the above-identified patent and that said Letters Patent is hereby corrected as shown below:

Col. 18, line 63, claim 1, in the definition of $R_2$, delete "α-Ala" and insert --β-Ala--.

Col. 19, line 7, claim 1, last line, replace "or" with --and-- and replace "salt" with --salts--.

Col. 19, line 21, claim 4, the first and second lines, delete "R(n) where".

Col. 19, line 21, claim 4, in the definition of $R_1$, after "Nle" insert --or a bond--.

Col. 19, line 21, claim 4, in the definition of $R_2$, after "D-Ala," insert --or--.

Col. 20, line 9, claim 12, third line before "Y=NH$_2$" delete one occurance of "and".

Col. 20, line 46, claim 13, last line replace "or" with --and-- and replace "salt" with --salts--.

Signed and Sealed this

Nineteenth Day of January, 1993

Attest:

DOUGLAS B. COMER

Attesting Officer

Acting Commissioner of Patents and Trademarks